United States Patent [19]
Wiley et al.

[11] Patent Number: 5,171,266
[45] Date of Patent: * Dec. 15, 1992

[54] VARIABLE POWER INTRAOCULAR LENS WITH ASTIGMATISM CORRECTION

[76] Inventors: Robert G. Wiley, 4545 Brookside Rd., Toledo, Ohio 43615; William G. Martin, 3553 Ridgewood Rd., Toledo, Ohio 43606

[ * ] Notice: The portion of the term of this patent subsequent to Apr. 28, 2009 has been disclaimed.

[21] Appl. No.: 577,473

[22] Filed: Sep. 4, 1990

[51] Int. Cl.$^5$ ............................................... A61F 2/16
[52] U.S. Cl. ........................................................ 623/6
[58] Field of Search ............................................ 623/6

[56] References Cited

U.S. PATENT DOCUMENTS

| | | | |
|---|---|---|---|
| 4,277,852 | 7/1981 | Poler | 623/6 |
| 4,298,966 | 11/1981 | Barnet | 623/6 |
| 4,373,218 | 2/1983 | Schachar | 623/6 |
| 4,512,039 | 4/1985 | Lieberman | 623/6 |
| 4,564,267 | 1/1986 | Nichimoto | 350/379 |
| 4,575,373 | 3/1986 | Johnson | 623/6 |
| 4,601,545 | 7/1986 | Kern | 350/332 |
| 4,601,722 | 7/1986 | Kelman | 623/6 |
| 4,787,903 | 11/1988 | Grendahl | 623/6 |
| 4,816,031 | 3/1989 | Pfoff | 623/6 |

*Primary Examiner*—Randy C. Shay
*Attorney, Agent, or Firm*—Marshall & Melhorn

[57] ABSTRACT

An intraocular lens has a flexible lens body center portion formed from an optically clear material surrounded by an outer ring which is sensitive to an external force, such as a magnetic force. Utilizing the external force, the shape of the outer ring can be changed to elongate the lens body along a predetermined axis for correcting astigmatism. The outer ring can also be used to change the power of the lens by altering the spherical shape or curvature of the lens. Attached to one of the lens body and the ring is a plurality of actuator bodies of ferromagnetic material which are either permanently magnetized by the external force or are temporarily magnetized and the altered shape is retained by a shape retainer attached to the ring.

20 Claims, 5 Drawing Sheets

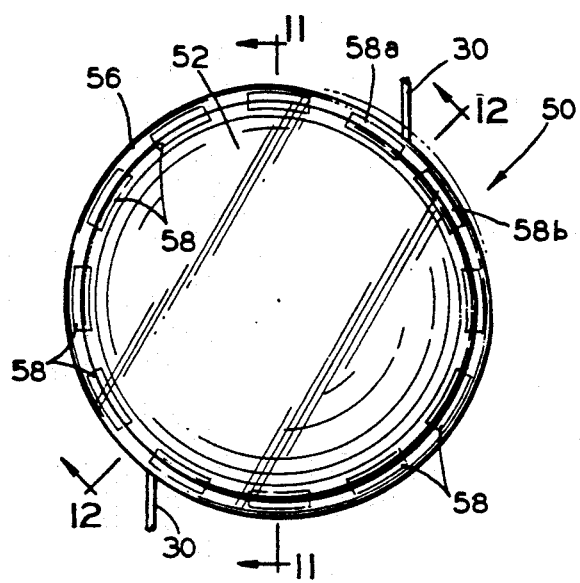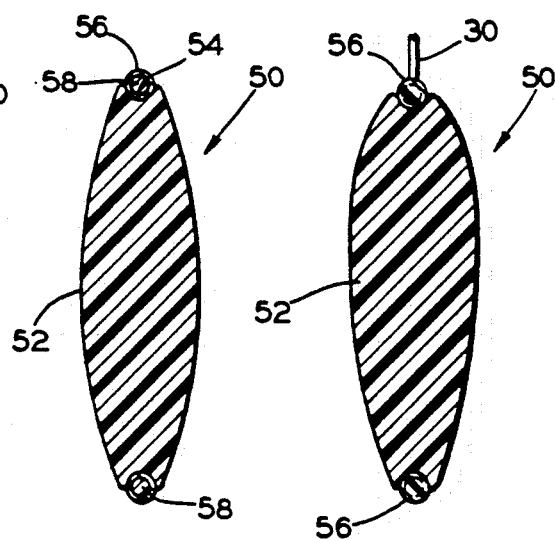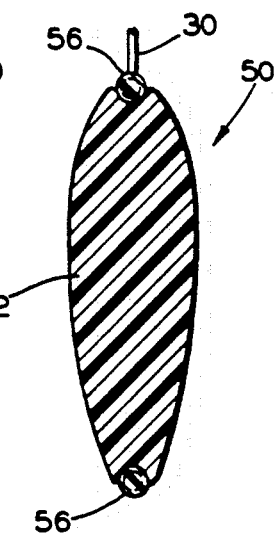
FIG. 10  FIG. 11  FIG. 12
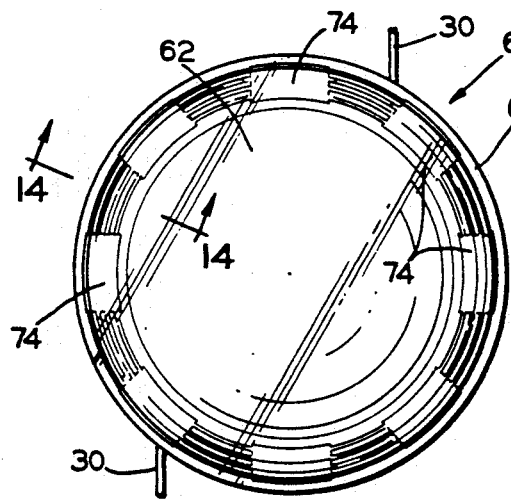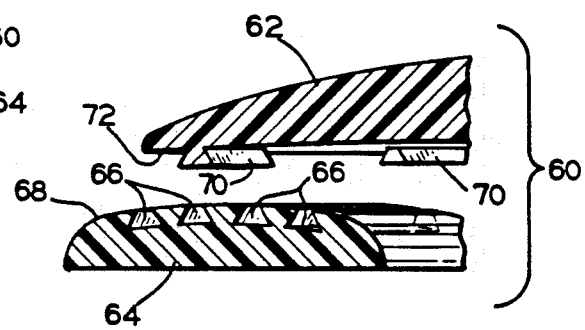
FIG. 13  FIG. 14
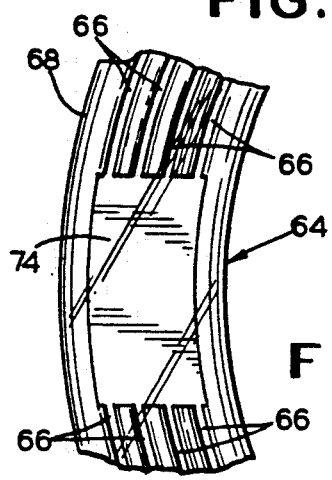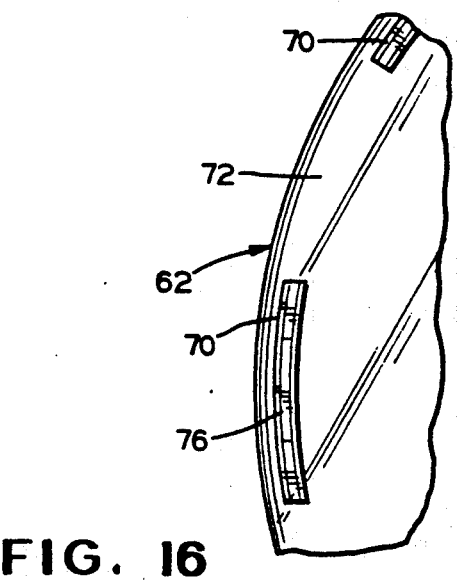
FIG. 15  FIG. 16

VARIABLE POWER INTRAOCULAR LENS WITH ASTIGMATISM CORRECTION

BACKGROUND OF THE INVENTION

The present invention relates generally to an intraocular lens and, in particular, to an apparatus for varying the power of and providing astigmatism correction in an intraocular lens.

The lens of the human eye is located centrally behind the pupil and is protected by the cornea. In the normal eye, the lens is clear and is substantially symmetrical, with opposed convex surfaces defining generally spherical sections. The lens and the cornea cooperate to focus light on the retina. The retina in turn cooperates with the nerves and the brain, so that light impinging on the retina is perceived as an image.

The light refraction which takes place in the cornea and the lens translates into an optical correction of about 60 diopters, with the cornea accounting for about 40 diopters and the lens accounting for about 20 diopters. Other refracting structures also are present in the eye, but are disregarded to simply the subject explanation.

A cataract is a condition where the normally clear lens of the eye becomes progressively opaque. This opacification typically occurs over an extended period of time, and the amount of light which passes through the lens decreases with increasing degrees of opacity. As the ability of the cataract lens to transmit light decreases, the ability of the eye to perceive images also decreases. Blindness ultimately can result. Since there are no known methods for eliminating the opacity of a cataract lens, it generally is necessary to surgically remove the opaque lens to permit the unobstructed passage of light through the pupil to the retina. The cataract lens is removed through a generally horizontal incision made at the superior part of the juncture where the cornea and sclera meet.

Once the lens has been surgically removed, light can be readily transmitted through the pupil and toward the retina. As noted above, the lens of the eye performs a significant light focusing function. Consequently, with the lens removed, the optical system of the eye is left about 20 diopters "short", and light is no longer properly focused on the retina. Eyeglasses, contact lenses and intraocular lenses are the three types of optical aids that commonly may be employed after cataract surgery to refocus the light on the retina.

Eyeglasses include lenses which are spaced from the cornea of the eye. The air space between the lens and the cornea causes an image magnification of more than 7%. Unfortunately, the brain cannot assimilate this magnification in one eye, and as a result an object appears double. This is a particular problem if the individual had only one cataract eye. Eyeglasses also substantially limit peripheral vision.

Contact lenses rest directly on the cornea of the eye, thus eliminating the air space. As a result, there is a much smaller image magnification with contact lenses than there is with eyeglasses, and the brain typically can fuse the images perceived by an eye with a contact lens and one without. Contact lenses, however, are less than perfect. For example, contact lenses are quite fragile and can be easily displaced from their proper position on the cornea. Additionally, the lenses must be periodically replaced because of protein build-up on the surface of the lens which can cause conjunctivitis. Furthermore, many of the elderly people who require cataract operations do not have the required hand coordination to properly remove or insert the lens.

Intraocular lenses first because available as optical aids to replace removed cataract lenses in about 1955. These lenses are placed in the eye, and thus closely simulate the optics of the natural lens which they are replacing. Unlike eyeglasses, there is virtually no image distortion with a properly made and placed intraocular lens. Also, unlike contact lenses, there is no protein build-up on the intraocular lenses and the lenses require no care by the patient.

To place the lens in the eye, the surgeon ordinarily makes an incision or opening in the cornea which aligns with the pupil, and the surgeon passes the lens through the opening. The attachment members of the lens are flexible and can be bent to pass through the opening. Accordingly, the minimum length of opening which must be made and is ordinarily determined by the diameter of the substantially rigid lens body, or optic, usually having a circular periphery. It is, of course, desirable to make the opening in the cornea as small as possible to minimize the risk of damage to the eye.

The current practice in the implantation of intraocular lenses is to replace a normal crystalline human lens of the eye removed at the time of surgery, such as in cataract surgery, with an intraocular lens such as an anterior chamber lens or posterior chamber lens formed of PMMA (polymethyl methacrylate) material. However, one of the present problems with intraocular lenses is that it is necessary to decide on the power of the lens preoperatively. This can be accomplished, for example, by performing an ultrasound scan and/or evaluating the patient's refraction preoperatively and then making a clinical estimate of the proper power of the lens in order to determine proper refraction of the eye. However, even with the best medical techniques and sophisticated optical instruments available, ophthalmologists have never been able to correctly predict for the accommodation of vision from distance to near vision and the power of the lens implant is not totally accurate for an individual who then still requires corrective lenses such as contacts or glasses.

The prior art intraocular lens typically is either of plano-convex construction or double convex construction, with each curved surface defining a spherical section. The lens is placed in the eye through the same incision which is made to remove the cataract lens. As noted above, this incision typically is made along the superior part of the eye at the juncture of the cornea and the sclera. The recipient of an intraocular lens typically will have clear vision with normal peripheral vision if there is no astigmatism. However, about one third of all patients who have vision problems have astigmatism and, in virtually all instances, the surgery itself induces astigmatism which fluctuates significantly during the first few weeks, or even months, after the surgery.

Postoperative induced astigmatism is attributable to the healing characteristics of the eye adjacent the incision through which the cataract lens is removed and the intraocular lens is inserted. More particularly, the sutured incision in the eye tends to heal more slowly and less completely as compared to incisions in the skin. For example, a sutured incision in skin typically heals in five to seven days, whereas a comparable incision in the eye may take eight weeks to a year to properly heal depending on the method of suturing. This slow healing rate is attributable to the nature of the eye tissue, poor vascularity and topical cortisone use after surgery. During the period when the eye is healing, the sutured area tends to spread and thus the prior spherical cornea is made other than spherical. Since the incision is generally horizontally aligned, the spreading is generally along the vertical meridian. Consequently, the optical system of the eye, which may previously have been spherical, becomes "toric" with the vertical meridian of the optical system providing a different optical power than the horizontal meridian. This non-spherical configuration of the optic system is generally referred to as "astigmatism".

The degree of this induced astigmatism varies according to the type of sutures used, the suturing technique and the technical skill and care employed by the surgeon, and the physical attributes of the eye. For example, the use of a fine nylon suturing material typically results in a smaller deviation from sphericity than the use of silk or absorbable suture. Generally, the induced astigmatism varies from 0.5 to 5 diopters. Although, the astigmatism resulting from the operation is generally in or near the vertical meridian, the orientation and deviation is not predictable. The induced astigmatism typically is corrected by prescription eyeglasses.

In some cases, despite the best efforts of the ophthalmologist, the lens surgically placed in the patient's eye does not provide good distance visual acuity. Furthermore, presently available intraocular lens do not correct the astigmatism refractive errors. Since most of the astigmatism present after cataract surgery is due to the surgical incision and changes in corneal curvature attendant to the incision's healing, the exact amount of astigmatism can not be accurately determined until sometime, usually several weeks, after the surgery. Since the old intraocular lens can not be readily removed and a new intraocular lens with a different power surgically installed without unduly jeopardizing the patient's vision, the patient must rely on spectacles to provide good distance visual acuity. In other words, although the need to wear heavy, bulky, higher power spectacles is eliminated, the patient may nevertheless be required to wear spectacles on a full time basis for good vision.

Several attempts have been made to provide an intraocular lens which corrects for the astigmatism expected after surgery or can be varied in power after implantation. U.S. Pat. No. 4,575,373 discloses a laser adjustable intraocular lens which utilizes a laser to alter, in situ, the power of an implanted intraocular lens. The outer ring of the lens is manufactured of a non-toxic heat shrinkable colored plastic material to permit selective absorption of laser energy, thereby causing the shape of the lens to change increasing the power non-reversibly.

U.S. Pat. No. 4,816,031 discloses an intraocular lens system including a PMMA lens implant, a second soft and pliable lens positioned thereover, and electromechanical circuitry for regulating the distance between the two lenses, thereby providing for adjustment of the focal point of the lens system.

U.S. Pat. No. 4,787,903 discloses an intraocular lens including an annular Fresnel lens having a composite material overlaying the Fresnel elements. The index of refraction of the composite material changes when the material is excited with electrical power or radiant energy.

U.S. Pat. No. 4,601,722 discloses an intraocular lens having a lens body formed of a plurality of lens body portions and magnet means for the assembly of the portions into the lens body within the eye after the portions are individually inserted through an incision in the eye.

U.S. Pat. No. 4,601,545 discloses a variable power lens system including an optically active molecular material such as liquid crystals. A variable gradient index of refraction is achieved by applying a controlled stimulus field, such as a geometrically configured matrix of electrical voltages, to the lens.

U.S. Pat. No. 4,564,267 discloses a variable focal length lens wherein the focal length can be electrically controlled by applying an electric field to a compound lens including at least one lens formed of electrooptic crystal.

U.S. Pat. No. 4,512,039 discloses an intraocular lens for offsetting postoperative astigmatism having the finally placed vertical meridian optically weaker than the horizontal meridian. Proper placement is ensured by disposing the haptics along the vertical meridian.

U.S. Pat. No. 4,373,218 discloses a variable power intraocular lens including a fluid expandable sac for containing a liquid crystal material that is used in combination with an electrode and a microprocessor for changing the index of refraction of the lens.

U.S. Pat. No. 4,298,996 discloses a magnetic retention system for an intraocular lens having one or more supports extending from the lens body. Each support carries a pair of magnetic fixation members positioned on opposite sides of the iris, whereby a trans-iris magnetic force secures the lens in place without sutures or incisions in the iris.

U.S. Pat. No. 4,277,852 discloses an intraocular lens with astigmatism correction combined with a supporting mount or haptic structure to assure correct optical orientation of the implant.

SUMMARY OF THE INVENTION

In recent years, exploratory surgery and radiography have been replaced by magnetic resonance imaging (MRI) as a method of seeing inside the human body. The body is subjected to a powerful magnetic field which aligns the atoms of the body in a north-south orientation. An FM radio signal is transmitted through the body vibrating the molecules until they flip upside down. When the radio signal is terminated, the molecules flip back turning each atom into a tiny FM radio station whose signals are detected by an MRI scanner. It is an object of the present invention to change the focal power and astigmatism correction of a lens in an eye, in much the same manner as MRI, by applying an external force field which aligns actuating means in the lens.

The present invention concerns an intraocular lens having a flexible lens body center portion formed from an optically clear material surrounded by an outer ring which is sensitive to an external force field, such as a magnetic force. Utilizing the external force field, the shape of the outer ring can be changed to elongate the lens body along a predetermined axis for correcting astigmatism. The outer ring can also be used to change the power of the lens by altering the spherical shape of the lens.

In general, an intraocular lens apparatus, according to the present invention, for implantation into an eye includes an optically clear, flexible, generally circular lens body having a periphery; a relatively rigid ring having an inner periphery attached to the periphery of the lens body; and actuating means attached to one of the lens body and the ring for selectively and reversibly altering a shape of the lens body and maintaining an altered shape to adjust one or more characteristics of the lens body including the power and astigmatism correction, the actuating means being responsive to a presence of an external force field for altering the shape of the lens body.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 10 is a front elevational view of an intraocular lens apparatus in accordance with a second alternate embodiment of the present invention;

FIG. 11 is a cross-sectional view of the lens apparatus shown in the FIG. 10 taken along the line 11—11;

FIG. 12 is a cross-sectional view of the lens apparatus shown in the FIG. 10 taken along the line 12—12;

FIG. 13 is a front elevational view of an intraocular lens apparatus in accordance with a third alternate embodiment of the present invention;

FIG. 14 is a cross-sectional view of the periphery of the lens apparatus shown in the FIG. 13 taken along the line 14—14;

FIG. 15 is an enlarged fragmentary view of a portion of the ring of the lens apparatus shown in the FIG. 14;

FIG. 16 is an enlarged fragmentary rear elevational view of the flexible lens body of the lens apparatus shown in the FIG. 14;

DESCRIPTION OF THE PREFERRED EMBODIMENT

Figure 1:
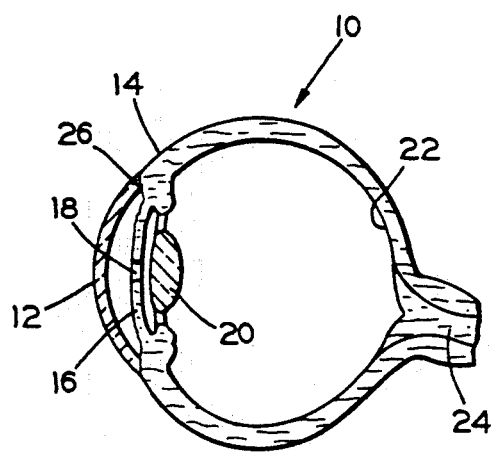
FIG. 1 is a cross-sectional side elevational view of a normal human eye prior to removal of the natural lens.

Referring to the FIG. 1, there is illustrated a normal human eye generally indicated by the reference numeral 10. The eye 10 includes a cornea 12 covering an opening in a generally spherical sclera 14. Positioned interiorly of the cornea 12 in the opening in the sclera 14 is an iris 16 having a pupil 18. Positioned behind the pupil 18 is a lens 20 which focuses entering light onto a retina 22 on the interior surface of the eye, the retina being connected to the brain (not shown) by an optic nerve 24. The lens 20 is located centrally behind the pupil 18 and is protected by the cornea 12. In the normal eye 10, the lens 20 is clear and is substantially symmetrical, with opposed convex surfaces defining generally spherical sections. The lens 20 and the cornea 12 cooperate to focus incoming light on the retina 22. The retina 22 in turn cooperates with the optic nerve 24 and the brain, so that light impinging on the retina 22 is perceived as an image.

The light refraction which takes place in the cornea 12 and the lens 20 translates into an optical correction of about sixty diopters, with the cornea 12 accounting for about forty diopters and the lens 20 accounting for about twenty diopters. Other refracting structures also are present in the eye 10, but are disregarded here to simplify the explanation.

A cataract is a condition where the normally clear natural lens 20 of the eye 10 becomes progressively opaque. This opacification typically occurs over an extended period of time, and the amount of light which passes through the lens 20 decreases with increasing degrees of opacity. As the ability of the cataract lens 20 to transmit light decreases, the ability of the eye 10 to perceive to images also decreases. Ultimately, blindness can result. Since there are no known methods for eliminating the opacity of a cataract lens 20, it generally is necessary to surgically remove the opaque lens 20 to permit the unobstructed passage of light through the pupil 18 to the retina 22. The cataract lens 20 is removed through a generally horizontal incision made at the superior part of a juncture 26 where the cornea 12 and the sclera 14 meet.

Figure 2:
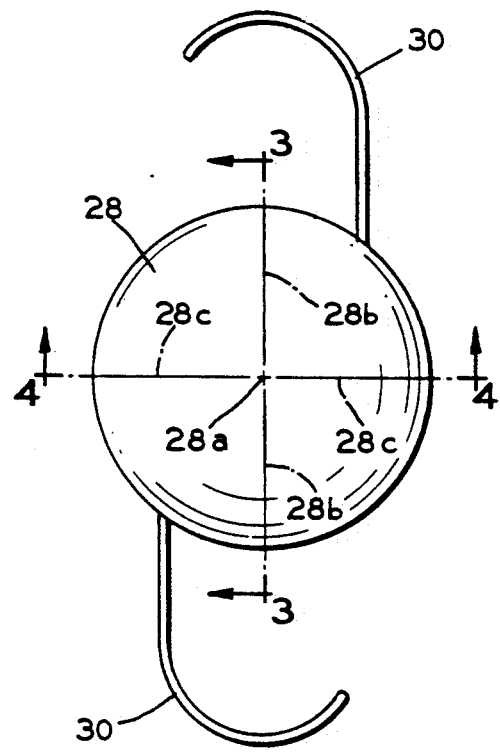
FIG. 2 is a front elevational view of a typical prior art intraocular lens.

Once the cataractous lens 20 has been surgically removed, light can be readily transmitted through the pupil 18 and toward the retina 22. However, the lens 20 performs a significant light focusing function. Consequently, with the lens 20 removed, the optical system of the eye is left about twenty diopters "short", and light is no longer properly focused on the retina 22. When a lens 20 is removed to eliminate cataracts, it must be replaced by an artificial lens. An intraocular lens, such as a prior art intraocular lens 28 shown in the FIG. 2, is commonly employed after cataract surgery to refocus the light on the retina 22.

Figure 5:
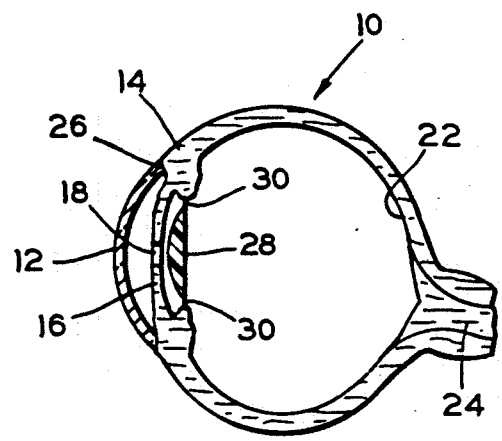
FIG. 5 is a cross-sectional side elevational view of the human eye shown in the FIG. 1 after the insertion of the intraocular lens shown in the FIG. 2.

The intraocular lens 28, which is constructed of any biologically inert, transparent material suitable for optical correction such as, for example, silicone, defines a toric section. The lens 28 is a section of a sphere, generally circular as viewed from the front with a diameter of approximately six millimeters. A pair of haptics 30 function as legs which support the lens 28 in the proper position in the posterior chamber of the eye 10 (FIG. 5). Each haptic 30 extends approximately four millimeters from a straight end attached to a periphery of the lens 28 to a curved end to be attached to the eye. Thus, the total width of the lens 28 and the haptics 30 is approximately fourteen millimeters.

The intraocular lens 28 is inserted behind the iris 16 as illustrated in the FIG. 5. This type of lens is referred to as a posterior chamber lens, the latest and most popular of the many designs of intraocular lenses.

It should be understood that the prior art lens 28 can be manufactured for positions in the eye other than the posterior chamber. For example, the lens 28 can be placed in the anterior chamber, the area intermediate the cornea 12 and the iris 16. However, such positioning is sometimes considered undesirable because positioning the lens very close to the cornea may result in traumatization of the endothelium.

A problem associated with the proper implantation of an intraocular lens is the accurate determination of the exact prescriptive or refractive power of the lens to be placed in the eye of the cataract patient. The ophthalmologist can, for example, attempt to measure the prescriptive power of the natural lens 20 of the patient and, through the use of various measuring devices. e.g. ultrasound, measure the depth and diameter of the eye 10. These measurements in conjunction with clinical experience permit the ophthalmologist to relatively accurately determine the proper refraction or power of the intraocular lens 28 to be used.

In some cases however, despite the best efforts of the ophthalmologist, the lens surgically placed in the eye is not the correct dioptric power and the patient does not obtain good unaided visual acuity. During the postoperative healing period, the patient often develops an astigmatism, a refractive defect in the lens which prevents focusing of sharp distinct images. Some astigmatism present after cataract surgery is due to the surgical incision and changes in corneal curvature as a consequence of the healing of the incision.

Figure 3:
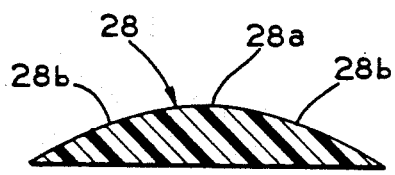
FIG. 3 is a cross-sectional view of the lens shown in the FIG. 2 taken along the line 3—3 on the vertical meridian.
Figure 4:
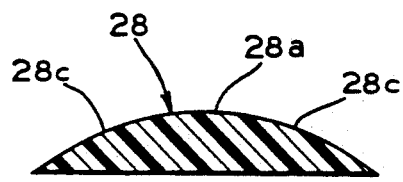
FIG. 4 is a cross-sectional view of the lens shown in the FIG. 2 taken along the line 4—4 on the horizontal meridian.

The curvature in the lens 28 can be formed asymmetric such that a vertical meridian, along a cross section line 3—3 as illustrated in the FIG. 3, is optically weaker than an horizontal meridian along a cross section line 4—4 as illustrated in the FIG. 4. The thickness of the lens 28 at a center 28a remains constant. Thus, the difference in the respective optical strengths of vertical and horizontal meridians is created by different structural contours (such as different radii of curvature), 28b and 28c, in the vertical and horizontal meridians respectively resulting in different light refracting characteristics. Thus, the lens 28 defines a toric section of a sphere. In order to properly align the lens 28 at the time of insertion in the eye, the haptics 30 are offset from and extend generally parallel to the vertical meridian.

Figure 6:
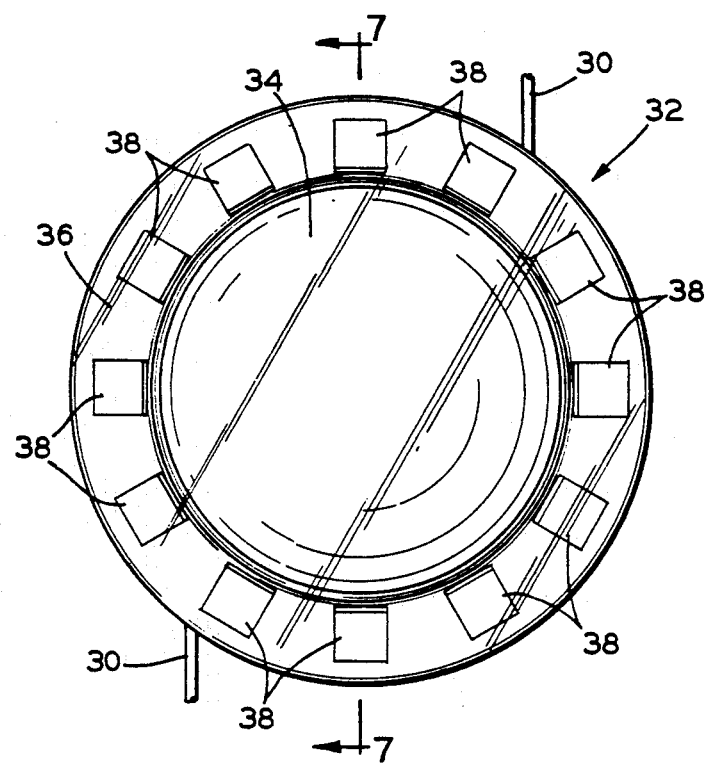
FIG. 6 is a front elevational view of an intraocular lens apparatus in accordance with the present invention.
Figure 7:
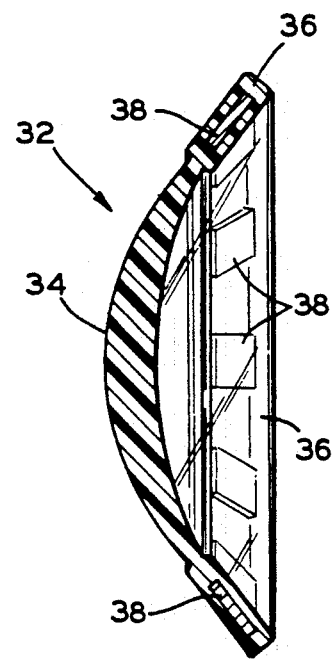
FIG. 7 is a cross-sectional view of the lens apparatus shown in the FIG. 6 taken along the line 7—7.

Thus, the prior art intraocular lens 28 has a fixed correction for astigmatism and a fixed power. In the FIGS. 6 and 7, there is shown an intraocular lens apparatus 32 which, according to the present invention, is provided with means for selectively changing the power of the lens and means for selectively providing correction for astigmatism. The lens apparatus 32 includes a central lens body 34 formed of a transparent flexible material and attached about a periphery thereof to an inner periphery of a ring 36 formed of a more rigid material. A pair of the haptics 30 can be attached to the ring 36.

Actuating means, in the form of a plurality of actuator bodies 38 are equally spaced about the circumference of the ring 36. The bodies 38 can be attached to a surface of the ring 36 or embedded when the ring is formed. The bodies 38 are formed of a magnetizable material such that each individual body functions as a permanent magnet having a north pole and a south pole. If adjacent ones of the bodies 38 are magnetized to repel, the ring 36 will be expanded and increase in circumference causing the lens body 34 to become less convex and, therefore, weaker in power. If adjacent ones of the bodies 38 are magnetized to attract, the ring 36 will be contracted and decrease in circumference causing the lens body 34 to become more convex and, therefore, stronger in power. Thus, the actuator bodies 38 can be utilized to selectively control the power of the lens apparatus 32 after installation in the eye and will retain the selected shape of the lens body 36 until reset.

The degree of the astigmatism is readily determinable through the use of conventional methods. An external magnetic force can then be applied to predetermined ones of the bodies 38 to expand or contract a portion of the ring 36 aligned with the astigmatism to create the necessary toric shape.

The magnetic force required to magnetize the bodies 38 should be sufficient to prevent exposure to normal level everyday magnetic forces from resetting the lens 32.

Figure 8:
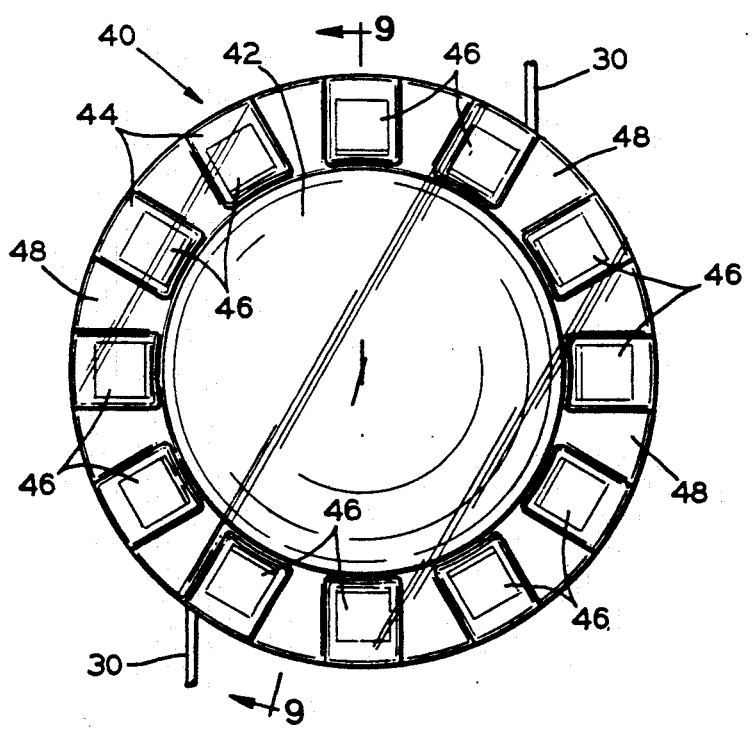
FIG. 8 is a front elevational view of an intraocular lens apparatus in accordance with a first alternate embodiment of the present invention.
Figure 9:
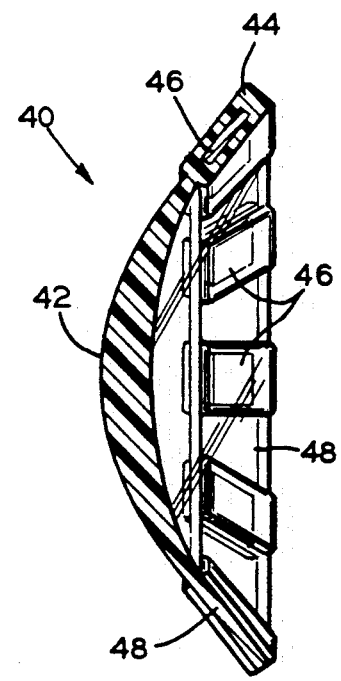
FIG. 9 is a cross-sectional view of the lens apparatus shown in the FIG. 8 taken along the line 9—9.

In the FIGS. 8 and 9 there is shown an alternate embodiment of the present invention. A lens apparatus 40 has a flexible central lens body 42 attached at a periphery thereof to an inner periphery of a more rigid ring 44. A plurality of magnetizable actuator bodies 46 are equally spaced about the ring 44 for selectively changing the power and the astigmatism correction as discussed with respect to the lens apparatus 32. However, portions 48 of the ring 44 positioned between the bodies 46 are formed with a reduced thickness as compared with adjacent portions which enclose the bodies. Thus, additional flexibility of the ring is achieved requiring less force to compress or expand the ring and change the shape of the lens body. A pair of the haptics 30 can be attached to the ring 44.

The lens bodies 34 and 42 of the lens assemblies shown in the FIGS. 6-9 have a convex surface facing toward the pupil 18 and a concave rearwardly facing surface. Alternatively, a second alternate embodiment is shown in the FIGS. 10-12 as a lens apparatus 50 having convex front and rear surfaces. A lens body 52 is formed from a transparent, somewhat flexible material with a circular shape in plan view and an ellipsoid shape in edge view. An annular groove 54 extends about the periphery of the body 52. Positioned in the groove 54 is a ring 56 having a plurality of magnetizable actuator bodies 58 embedded therein. If all adjacent actuator bodies are magnetized to attract or repel, the ring 56 will contract or expand respectively equally in all portions to selectively change the shape of the lens thereby changing the power of the lens. Also, two or three adjacent magnets can be magnetized to produce an astigmatism correction, either at opposite ends of a diameter to correct for regular astigmatism as illustrated in the FIG. 11, or at one end of the diameter to correct for irregular astigmatism as illustrated in the FIG. 12. A pair of adjacent bodies 58a and 58b have been magnetized to attract thereby changing the shape of the upper portion of the lens body 52 along the line 12—12 in the FIG. 10. A pair of the haptics 30 can be attached to the ring 56.

A third alternate embodiment is shown in the FIGS. 13-16 as a lens apparatus 60 having a flexible or malleable material (such as silicone) lens body 62 releasably attached to a rigid material (such as PMMA) ring 64. A pair of the haptics 30 can be attached to the ring 64. A plurality of spaced apart different diameter circumferential grooves 66 are formed in a forwardly facing surface 68 of the ring 64. The lens body 62 has a circumferential tongue 70 formed on a rearwardly facing surface 72 thereof. The grooves 66 and the tongue 70 can be formed with any suitable cross-sectional shape, such as the trapezoidal shape illustrated, provided that the grooves firmly retain the tongue to prevent separation of the lens body 62 from the ring 64. The power of the flexible or malleable lens body 62 can be changed selectively by moving the tongue 70 to an appropriate one of the grooves 66, the outermost one of the grooves resulting in the lowest power and the innermost one of the grooves resulting in the highest power. Movement between the grooves is accomplished by forming the grooves 66 with a plurality of interruptions or adjustment spaces 74. In a similar manner, the tongue 70 is segmented with each segment corresponding in position to and being of no greater length than one of the adjustment spaces 74.

The lens apparatus 60 can be preset for any desired power prior to insertion in the eye by aligning the tongue 70 with a selected one of the grooves 66 and rotating lens body 62 with respect to the ring 64 to insert the tongue into that groove. If a change in power is required, the lens body 62 is rotated to align the segments of the tongue 70 with the adjustment spaces 74 the tongue is moved to the selected one of the grooves 66 for the power desired and the tongue is rotated into the newly selected grove. The entire tongue 70 can be formed of a magnetically responsive material or an actuator body 76 (FIG. 16) formed of magnetically responsive material can be embedded in each segment of the tongue. An external magnetic field can be utilized to move each of the actuator bodies 76.

Figure 17:
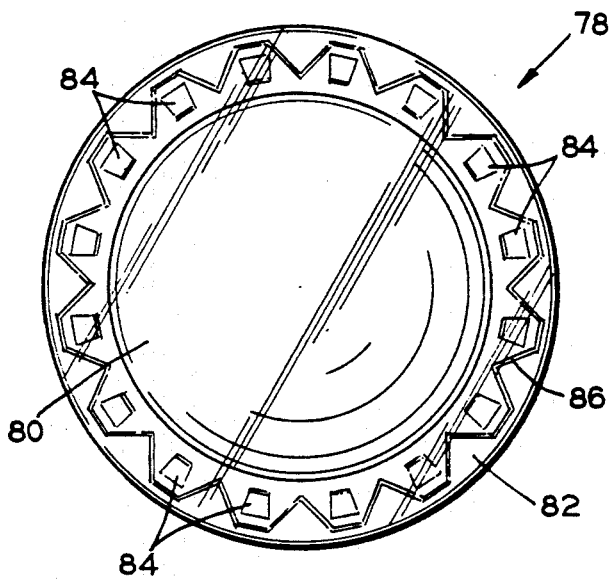
FIG. 17 is a front elevational view of an intraocular lens apparatus in accordance with a fourth alternate embodiment of the present invention.
Figure 18:
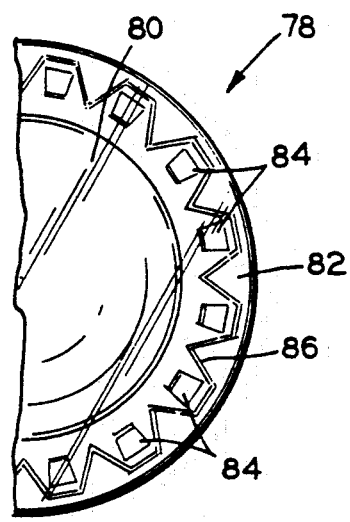
FIG. 18 is a fragmentary front elevational view of the lens apparatus shown in the FIG. 17 set for increased power.

In the FIGS. 17 and 18, there is shown a fourth alternate embodiment of the present invention. A lens apparatus 78 includes a central lens body 80 attached at a periphery thereof to an inner periphery of a more rigid ring 82. A plurality of magnetizable actuator bodies 84 are equally spaced about the ring 82 for selectively changing the power and the astigmatism correction. The bodies 84 can be embedded in the ring 82 together with a means for retaining the shape of the lens apparatus 78 such as a shape retainer 86 formed of wire. The wire 86 extends circumferentially through the ring 82 between the bodies 84 and an outer periphery of the ring. A portion of the wire 86 between each of the adjacent pairs of bodies 84 extends inwardly toward the center of the lens apparatus 78 and turns sharply outwardly in a V-shape. If an external electromagnetic force is applied to a pair of adjacent ones of the bodies 84 tending to move the bodies together contracting the ring 82, at the same time, the V-shaped portion in the wire 86 between the adjacent bodies is made narrower. When the external force is removed, the wire 86 holds its new shape until the adjacent bodies 84 are moved again even if the bodies are not permanently magnetized. Thus, all of the bodies 86 can be moved to compress or expand the ring 82 thereby increasing and decreasing respectively the power of the lens apparatus 78. Furthermore, selected ones of the bodies 84 can be acted upon to produce astigmatism correction in the desired area of the lens apparatus 78. An example of the ring 82 contracted from the shape shown in the FIG. 17 is shown in the FIG. 18.

Figure 19:
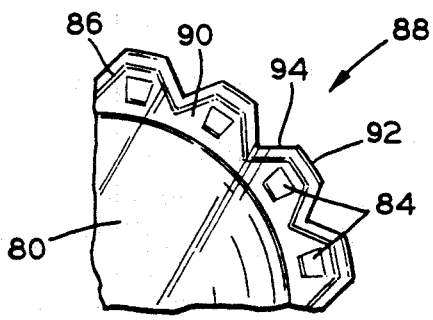
FIG. 19 is a fragmentary front elevational view of an intraocular lens apparatus in accordance with a fifth alternate embodiment of the present invention.

In FIG. 19, there is shown a fifth alternate embodiment of the present invention. A lens apparatus 88 includes the lens body 80 from the previous embodiment attached at a periphery thereof to an inner periphery of a ring 90. The ring 90 has embedded therein a plurality of the actuator bodies 84 and the shape retainer 86. An outer periphery 92 of the ring 90 has a plurality of V-shaped notches 94 formed therein adjacent the V-shaped portions of the shape retainer 86 in order to render the ring 90 more responsive to compression and stretching. Thus, the ring 90 is more flexible, requiring less force to contract or expand than the previously described ring 82.

Figure 20:
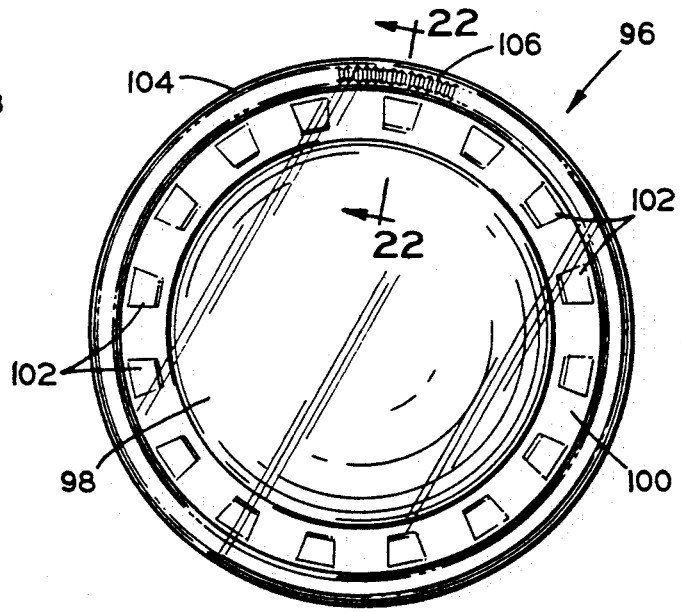
FIG. 20 is a front elevational view of an intraocular lens apparatus in accordance with a sixth alternate embodiment of the present invention.
Figure 21:
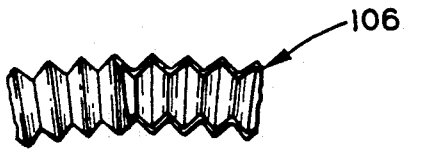
FIG. 21 is an enlarged fragmentary view of the selectively adjustable shape retainer included in the lens apparatus shown in the FIG. 20.
Figure 22:
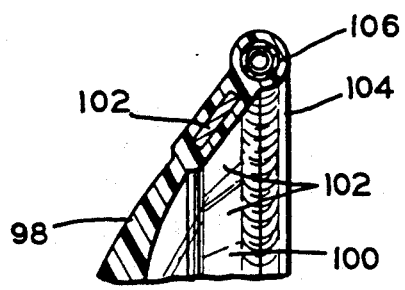
FIG. 22 is a cross sectional view of a portion of the periphery of the lens apparatus shown in the FIG. 21 taken along the line 22—22.

There is shown in FIGS. 20-22, a sixth alternate embodiment of the present invention. A lens apparatus 96 has a flexible central lens body 98 attached at a periphery thereof to an inner periphery of an inner ring 100. A plurality of magnetizable actuator bodies 102 are equally spaced about the ring 100 for selectively changing the power and the astigmatism correction as discussed with respect to the other lens assemblies above. However, an outer periphery of the inner ring 100 is attached to an inner periphery of an outer ring 104 having a shape retainer 106 embedded therein. The shape retainer 106, as more clearly seen in FIG. 21, is of tubular shape and acts in an accordion fashion to lengthen and shorten. When two adjacent ones of the actuator bodies 102 are moved toward one another or away from one another, the inner ring 100 and the outer ring 104 tend to contract and expand respectively. The shape retainer 106 is also contracted or expanded and is formed of a material which retains its position until it is again forced to move by the bodies 102. Thus, the power and the astigmatism correction for the lens 96 can be controlled through the movement of the actuator bodies 102 and the shape retention capabilities of the shape retainer 106.

Figure 23:
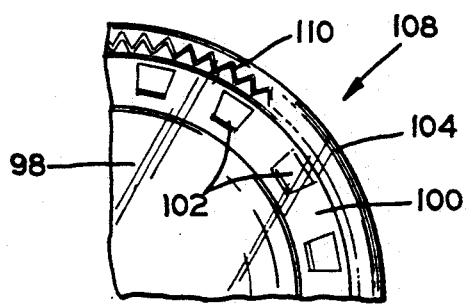
FIG. 23 is a fragmentary front elevational view of an intraocular lens apparatus in accordance with a seventh alternate embodiment of the present invention.

There is shown in FIG. 23, a seventh alternate embodiment of the present invention based upon the lens apparatus 96 shown in FIG. 20. A lens apparatus 108 utilizes the lens body 98, the inner ring 100, the actuator bodies 102 and the outer ring 104 as described above. However, the shape retainer 106 has been replaced with a helically formed wire shape retainer 110 which retains its shape once set by the movement of the actuator bodies 102.

Figure 24:
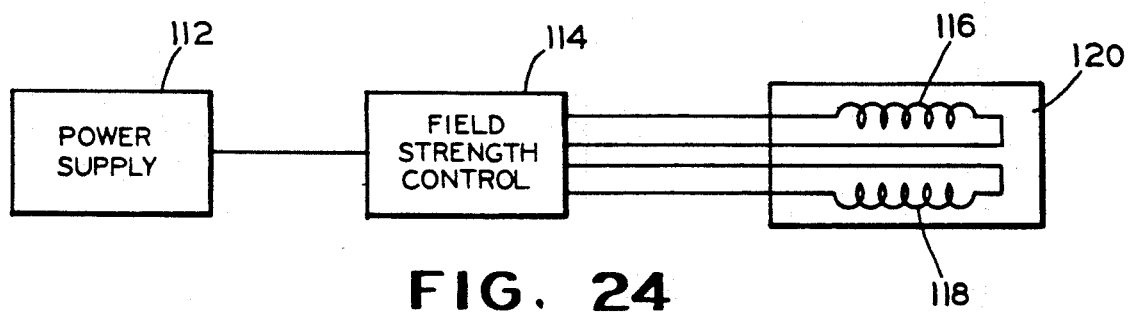
FIG. 24 is a schematic block diagram of a basic control apparatus for operating the actuator bodies in each of the lens assemblies according to the present invention.

There is shown in the FIG. 24 a block diagram of a control system for operating the actuator bodies in each of the above-described lens assemblies. A power supply 112 has an output connected to an input of a field strength control 114. An output of the field strength control 114 is connected to a first coil 116. A second output of the field strength control 114 is connected to a second coil 118. Each of the coils 116 and 118 can be mounted on a holder 120. The holder is any suitable device for positioning the coils 116 and 118 adjacent associated ones of the actuator bodies in any of the above-described lens assemblies. The field strength control 114 is selectively adjustable for applying a wide range of electrical power to each of the coils 116 and 118 individually in order to either permanently magnetize or simply move the associated body in accordance with the method of operation of one of the lens assemblies according to the present invention. The coils 116 and 118 are representative of either a single coil which can be separately aligned with each of the actuator bodies in turn or any other number of such coils including a separate coil for each of the actuator bodies such that all of the actuator bodies in a lens apparatus can be operated at the same time.

Figure 25:
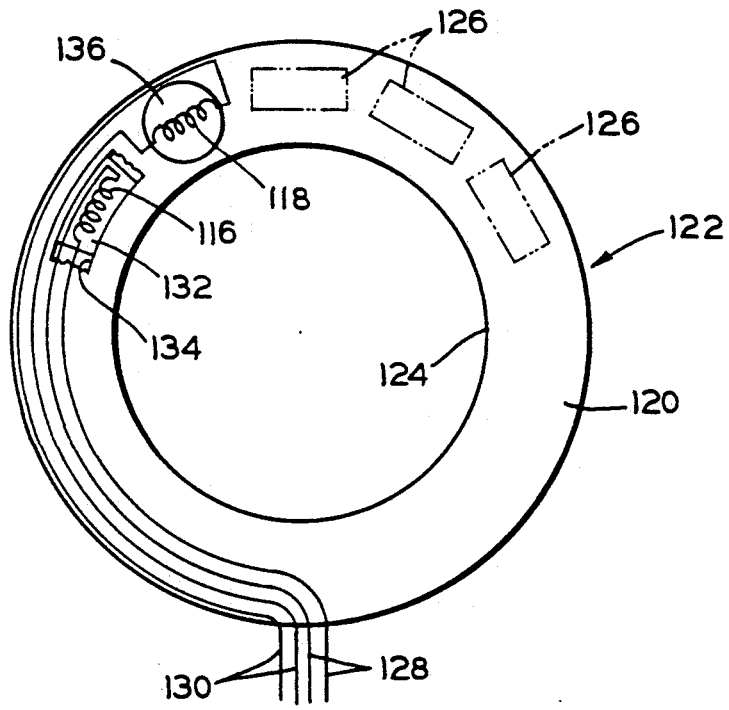
FIG. 25 is a front elevational view of an instrument used with the control apparatus shown in the FIG. 24.

As shown in the FIG. 25, the holder 120 can form a portion of an instrument 122 for operating the actuator bodies of a lens apparatus according to the present invention. The holder 120 can be ring-shaped having a center aperture 124 which can be utilized to align the instrument 122 with one of the lens assemblies according to the present invention installed in the human eye. Mounted on the ring-shaped holder 120 are the coils 116 and 118, each of the coils being positioned in alignment with an associated one of the actuator bodies in the lens apparatus to be operated. Additional coils 126 mounted on the holder 120 are shown schematically and represent any desirable number of such coils. The coil 116 is connected by a pair of lead wires 128 to any suitable control such as the field strength control 114 shown in FIG. 24. Similarly, the coil 118 is connected by a pair of lead wires 130 to a suitable control.

The polarity of the magnetic field generated by the coils 116 and 118 can be reversed by simply reversing the current flow through the associated wires 128 and 130. The coils 116 and 118 can also be provided with mechanical means for orienting them to selectively operate the actuator bodies in a desired manner. For example, the coil 116 can be mounted on a carrier 132 slidably retained in a circumferentially extending slot 134 formed in a face of the holder 124. The carrier 132 can be moved in either direction along the slot 134 to accurately position the coil 116 with respect to an associated actuator body. Alternatively, the coil 118 is shown mounted on a circular carrier 136 which is rotatably mounted on the holder 120. Thus, the angular orientation of the coil 118 with respect to a radius of the holder 120 can be selectively changed as desired.

The instrument 122 can be incorporated into a device which can be utilized by the patient to change the shape of the lens body as the situation requires. For example, the instrument 122 can be built into a pair of eyeglasses or formed as a handheld control and operated by the patient to change the lens focus between near vision and far vision.

Figure 26:
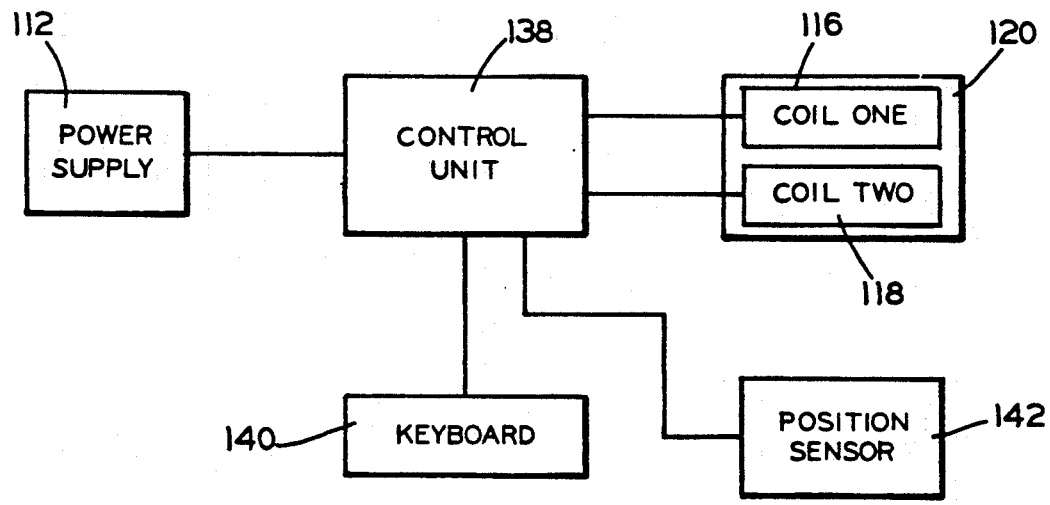
FIG. 26 is a schematic block diagram of an automated control apparatus for operating the instrument shown in the FIG. 25 and the actuator bodies in each of the lens assemblies according to the present invention.

There is shown in the FIG. 26 a control for automatically operating the actuator bodies of any of the above-described lens assemblies according to the present invention. The previously described power supply 112 is connected to an input of a control unit 138. A pair of outputs of the control unit 138 are connected to the coils 116 and 118 which are mounted on the holder 120. The control unit 138 can include a general purpose, programmed microprocessor having a standard operating software system and a program for receiving instructions through a keyboard 140 connected to an input of a control unit 138 as to the strength and duration of the electrical power to be applied from the power supply 112 to the coils 116 and 118 in order to operate the actuator bodies as desired. In addition, a position sensor 142 can be connected to an input of the control unit 138 for generating a signal representing the position of the holder 120 and the coils 116 and 118 with respect to the lens apparatus to be operated. The position sensor 142 can be any suitable device, typically light sensitive, for detecting any of the physical features on the lens apparatus. For example, the position sensor 142 could detect the actuator bodies, a periphery of the lens body, or a periphery of the ring shown in any of the preceding lens apparatus embodiments.

The actuator bodies can be formed of a ferromagnetic element or one of a variety of alloys of ferromagnetic and other elements which respond to a nearby magnetic field. In some cases, the actuator elements can be "permanently" magnetized, magnetized even though the external magnetic field is removed, or simply aligned in response to the alignment of the electromagnetic field where a shape retainer is employed.

In summary, an improved intraocular lens is provided to eliminate or reduce the post-operative regular and irregular astigmatism. The invention utilizes an intraocular lens having a flexible center lens body surrounded by an outer ring having actuator bodies sensitive to an external force such as a magnetic field. Through the implementation of an external magnetic force, the shape of the lens can be changed to elongate the lens along a predetermined axis for correcting astigmatism. If the axis of the astigmatism changes, the shape of the lens can be changed by reapplying the force along a different axis. The ring can also be utilized to change the power of the lens, by changing the spherical shape. The utilization of such an intraocular lens may eliminate the need of the recovering cataract patient to wear eye glasses or contact lenses. The elimination of the glasses or contact lenses amounts to an immense benefit to the recovering cataract patient, many of whom are elderly and have enough hardships without being burdened with wearing glasses or contact lenses. Furthermore, a source of the external force can be incorporated into a pair of eyeglasses, if needed, or a handheld device to be selectively operated by the patient for the accommodation of different focal lengths.

Although the actuator bodies have been described as formed of ferromagnetic material responsive to a magnetic field, such bodies could be formed of any suitable material responsive to electromagnetic or mechanical energy waves which cause the ring to compress and expand circumferentially.

The various lens apparatuses discussed above can be categorized as "active" or "passive" systems. The "active" systems (32, 46 and 50) require the application of a force field to the actuating means to selectively and reversibly alter the shape of the lens body. The actuating means then actively generates its own force field to maintain the selected shape. The "passive" systems (60, 78, 88, 96 and 108) also require the application of a force field to the actuating means to selectively and reversibly alter the shape of the lens body. However, the actuating means does not require any force field to maintain the selected shape. Any of the actuating means of the "active" systems and any of the actuating means of the "passive" systems in the embodiments shown and described can be substituted for each other as desired. Furthermore, any of the actuator segments shown can be mounted for rotation in the associated ring similar to the coil 116 and the carrier 136 shown in the FIG. 25. Such an actuator segment would remain magnetized and could be rotated by the instrument 122 to attract or repel an adjacent actuator segment or be oriented in a neutral position.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An intraocular lens apparatus for implantation into an eye comprising:
   an optically clear, flexible, generally circular lens body having a periphery;
   a ring having an inner periphery attached to said periphery of said lens body; and
   actuating means attached to one of said lens body and said ring for selectively and reversibly altering a shape of said lens body and maintaining an altered shape to adjust characteristics of said lens body including the characteristics of power and astigmatism, said actuating means being responsive to a presence of an external force field for altering said shape.

2. The lens apparatus according to claim 1 wherein said lens body is formed of silicone material and said ring is formed of polymethyl methacrylate material.

3. The lens apparatus according to claim 1 wherein said actuating means includes a plurality of ferromagnetic material actuator bodies equally spaced about the circumference of said ring.

4. The lens apparatus according to claim 3 wherein each of said actuator bodies is magnetized to attract or repel an adjacent one of said bodies whereby an attached portion of said ring is compressed or expanded respectively.

5. The lens apparatus according to claim 4 wherein said actuator bodies are permanently magnetized whereby the altered shape is maintained.

6. The lens apparatus according to claim 4 wherein said actuator bodies are temporarily magnetized to alter a shape of said ring and said lens body and said ring maintains the altered shape.

7. The lens apparatus according to claim 3 wherein said ring is thicker at said actuator bodies and is thinner between adjacent ones of said actuator bodies.

8. The lens apparatus according to claim 1 including an annular groove formed in said periphery of said lens body and wherein said ring is positioned in said groove.

9. The lens apparatus according to claim 1 wherein said ring has at least two circumferential grooves formed therein and said lens body has a tongue formed thereon, said tongue cooperating with said grooves to attach said lens body to said ring.

10. The lens apparatus according to claim 9 wherein said grooves are interrupted by a plurality of adjustment spaces formed in said ring and said tongue is formed in segments, each said segment being no longer than an associated one of said adjustment spaces.

11. The lens apparatus according to claim 9 wherein said grooves and said tongue are trapezoidal in cross section.

12. The lens apparatus according to claim 1 wherein said actuating means includes a plurality of ferromagnetic material actuator bodies equally spaced about the circumference of said ring and a shape retainer attached to said ring, said actuator bodies being responsive to a presence of an external magnetic field for altering said shape and said shape retainer maintaining said altered shape.

13. The lens apparatus according to claim 12 wherein said shape retainer is a wire embedded in said ring and having a plurality of generally V-shaped portions positioned between adjacent ones of said actuator bodies.

14. The lens apparatus according to claim 12 wherein said shape retainer is a helically coiled wire embedded in said ring.

15. The lens apparatus according to claim 1 including control means for operating said actuating means, said control means generating an external force field and said actuating means being responsive to said force field for altering said shape of said lens body.

16. The lens apparatus according to claim 15 wherein said control means includes a power supply connected to an input of a field strength control having an output connected to at least one coil for applying electrical power to said coil to generate a magnetic field adjacent to said actuating means.

17. An intraocular lens apparatus for implantation into an eye comprising:
    an optically clear, flexible, generally circular lens body having a periphery;
    a ring having an inner periphery attached to said periphery of said lens body; and
    a plurality of actuator means attached to one of said lens body and said ring for selectively and reversibly altering a shape of said lens body and maintaining an altered shape of said lens body to adjust characteristics of said lens body including the characteristics of power and astigmatism, said actuator means being responsive to a presence of an external force field for moving said ring to define said altered shape.

18. The apparatus according to claim 17 wherein said actuator means are formed of a ferromagnetic material and are permanently magnetized by an external magnetic force.

19. The apparatus according to claim 17 wherein said actuator means are formed of a ferromagnetic material and are temporarily magnetized by the external magnetic field and including a shape retainer attached to said ring for maintaining said altered shape.

20. An intraocular lens for implantation into an eye and control means for operating the lens apparatus for changing the power and astigmatism correction of the lens apparatus comprising:
    an optically clear, flexible central lens body;
    a ring having an inner periphery attached to a periphery of said lens body;
    electromagnetic energy responsive actuator means attached to one of said lens body and said ring for selectively and reversibly altering the shape of said lens body to adjust the power and astigmatism correction of said lens body; and
    a control means for generating a selectively variable force field for operating said actuating means, said actuating means being responsive to said force field for altering the shape of said lens body.

* * * * *